US00PP22495P3

(12) United States Plant Patent
Maillard et al.

(10) Patent No.: US PP22,495 P3
(45) Date of Patent: Feb. 14, 2012

(54) FLAT PEACH TREE NAMED 'ASFPBF0796'

(50) Latin Name: *Prunus persica*
Varietal Denomination: ASFPBF0796

(75) Inventors: Arsene Maillard, Elne (FR); Laurence Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 12/662,966

(22) Filed: May 13, 2010

(65) Prior Publication Data

US 2010/0293682 P1 Nov. 18, 2010

(30) Foreign Application Priority Data

May 18, 2009 (QZ) ..... PBR 2009/0935

(51) Int. Cl.
*A01H 5/00* (2006.01)

(52) U.S. Cl. ..... Plt./195

(58) Field of Classification Search ..... Plt./195
See application file for complete search history.

*Primary Examiner* — June Hwu
(74) *Attorney, Agent, or Firm* — Westerman, Hattori, Daniels & Adrian, LLP

(57) ABSTRACT

A new and distinct variety of flat peach tree, denominated 'ASFPBF0796', has fruits of very long shelf life without alteration before and after harvesting, a semi-sweet white flesh of high eating quality and an attractive red skin. Fruits can be consumed crunchy or melting.

4 Drawing Sheets

Botanical classification: *Prunus persica.*

Variety denomination: 'ASFPBF0796'.

This application claims priority of Community plant variety right No. 2009/0935 filed on May 18, 2009, which is hereby incorporated by reference in its entirety.

BACKGROUND OF THE NEW VARIETY

The present invention relates to a new and distinct variety of flat peach tree, *Prunus persica,* which has been given the variety denomination 'ASFPBF0796'. This new tree produces fruit with a long shelf life without alteration both on the tree after growth completion and after harvesting, very good eating quality, semi-clingstone white flesh fruit for fresh market in July in the Pyrénées-Orientales departement, France. Contrast is made to 'Nectarmagie' (U.S. Plant Pat. No. 17,579) white nectarine tree, 'ASFPBF0492' (U.S. Plant Pat. No. 21,143) white flat peach tree, 'Flatpretty' (U.S. Plant Pat. No. 21,389) white flat peach tree, standard varieties, for reliable description. 'ASFPBF0796' is a promising candidate for commercial success in that it has very attractive fruits with very long shelf life without alteration before after harvesting.

ORIGIN OF THE VARIETY

The 'ASFPBF0796' white flat peach tree originated in a cultivated area of the south of France, in the Pyrénées-Orientales departement, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontagne': it dries the air, clears the sky from clouds, but its intensity can be strong and affect the harvest, fruit quantity and/or quality. Marine moisture does not affect the place.

Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'ASFPBF0796' variety was selected from controlled crosses between the 'Nectarmagie' (U.S. Plant Pat. No. 17,579) white nectarine tree (female parent) and the 'ASFPBF0492' (U.S. Plant Pat. No. 21,143) white flat peach tree (male parent). Compared to the variety 'ASFPBF0798' (U.S. Pending Plant patent application Ser. No. 12/662,965), obtained with the same male and female parents, the 'ASFPBF0796' variety reaches maturity about 3 weeks earlier than 'ASFPBF0798'. 'ASFPBF0796' was provisionally designated, tested and genetically identified by a genetic profile, under number 01.29E.44 PBPL ASF 0796 and was registered at the Official Catalogue of the Agriculture Ministry of the French Republic on Dec. 1, 2008 under number 1028967. It was obtained by hybridizing and propagated by grafting on a 'Franc Inra Montclar' (non-patented) or 'Cadaman' (non-patented) or 'INRA GF 677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of peach tree blooms in March at Perpignan in the Pyrénées-Orientales departement, France. More particularly, it approximately blooms between the 1$^{st}$ and the 12$^{th}$ of March under normal climatic conditions, generally approximately 4 to 5 days earlier than the 'Flatpretty' (U.S. Plant Pat. No. 21,389) white flat peach tree The first fruit of 'ASFPBF0796' flat peach tree ripens during the last two weeks of July, generally about 10 to 12 days later than the 'Flatpretty' (U.S. Plant Pat. No. 21,389) white flat peach tree. More particularly, it approximately ripens between July 21$^{th}$ and July 31$^{th}$ under normal climatic conditions. The date of maturity varies slightly with the prevailing climatic conditions.

DESCRIPTION OF THE DRAWINGS

In the accompanying drawing, which are as nearly true as it is reasonably possible to make in a color illustration of this type.

Figure 1:
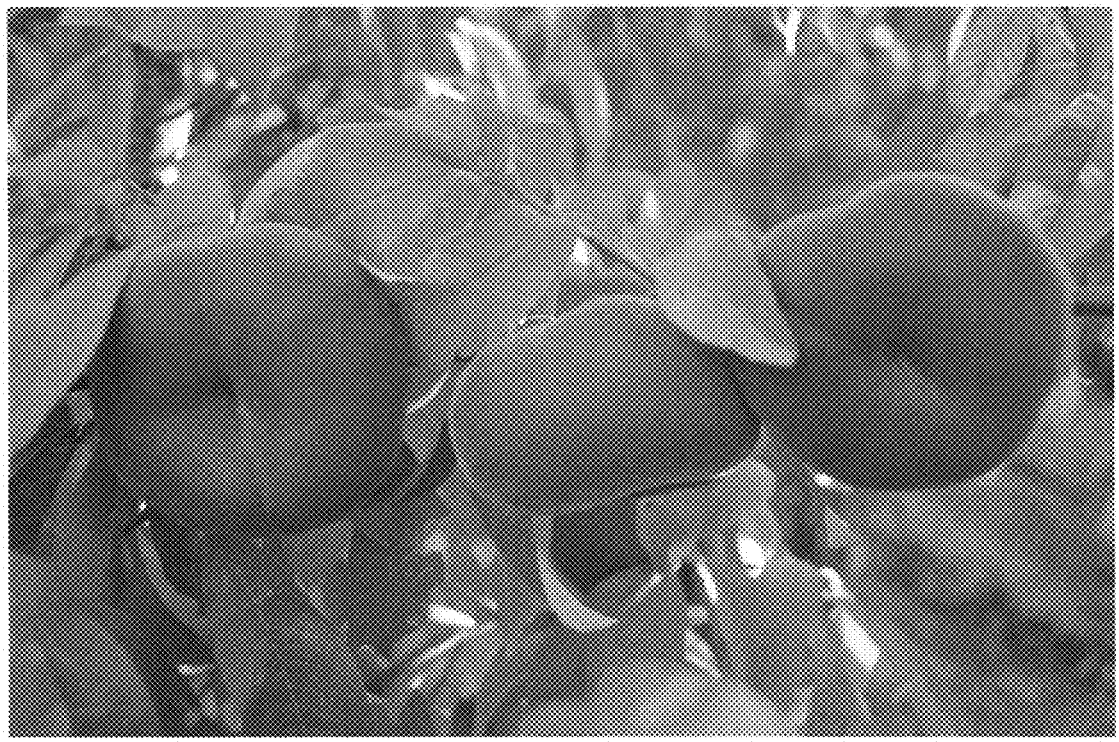
FIG. 1 is a color photograph which shows a branch bearing typical fruit specimens of the new variety, and leaves of the new variety, on a tree as found in our orchard.
Figure 2:
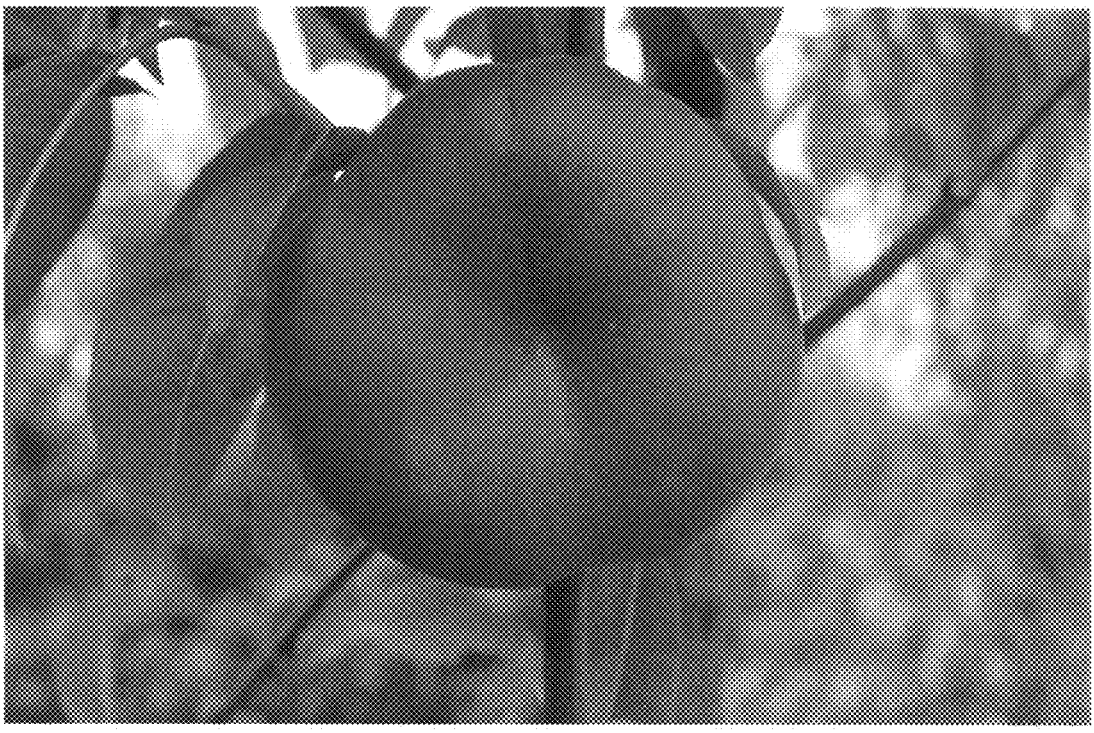
FIG. 2 is a color photograph which shows a branch bearing a typical fruit specimen of the new variety, on a tree as found in our orchard.
Figure 3:
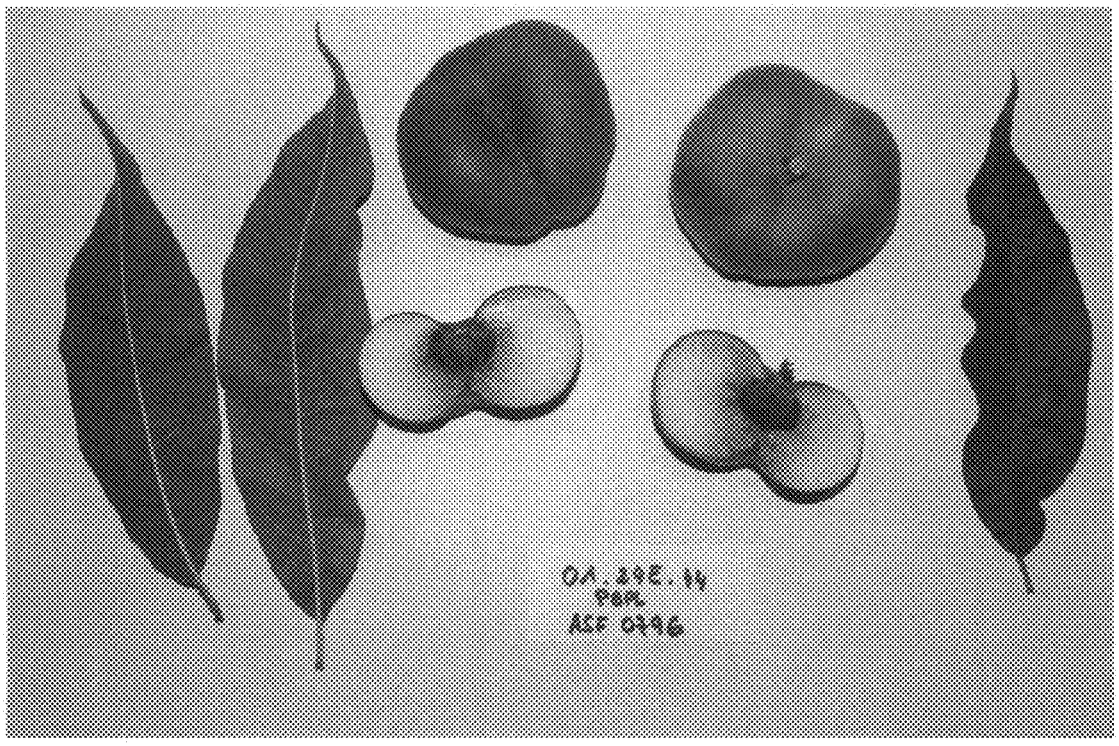
FIG. 3 is a color photograph which shows two whole fruits of the new variety and three leaves of the new variety, and a third fruit cut in half for depicting the fruit flesh, the pit cavity and the stone of the new variety.
Figure 4:
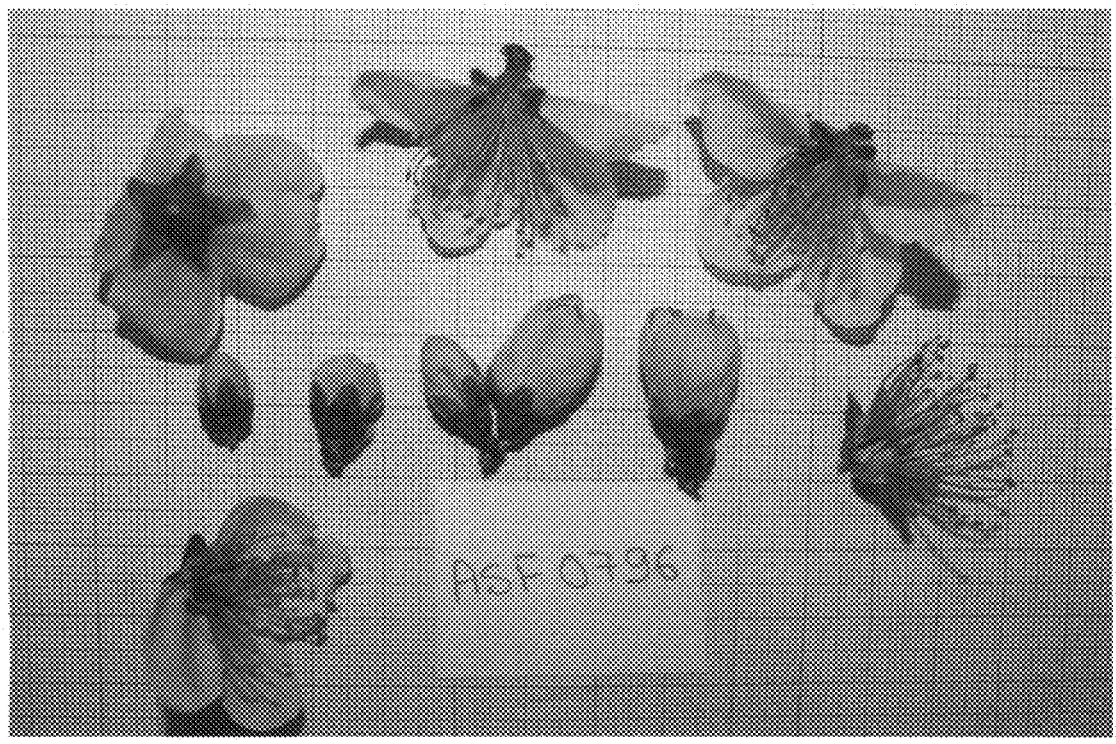
FIG. 4 is a color photograph with reverse and side views of flowers of the new variety, and, with petals removed, reproductive organs of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'ASFPBF0796' is high, due to fruit very long shelf life without alteration before and after harvesting.

Trees are vigorous and large stature half-standing in a semi-spread to semi-upright out aspect. The anthocyanic coloration of flowering shoot is present excluding brushwood side away from sun. Flowering begins semi-early to semi-late in springtime. The type of flower is showy with relative medium petal size. Petals are medium pink. Leaf glands are present and reniform. Time of maturity for consumption is semi-late. Fruits are flat. The fruit flesh is white and its skin is thick, with a luminous red blush color. The stone is small. Fruit taste is semi-sweet, very aromatic and with a high level of sugars.

The new variety ripens slightly later than its male parent, which is the 'ASFPBF0492' (U.S. Plant Pat. No. 21,143) white flat peach tree, usually ripening on July 22 under normal climatic conditions. Comparatively, the male parent produces fruits with a luminous pinky red coloration.

In comparison to its female parent, which is 'Nectarmagie' (U.S. Plant Pat. No. 17,579) white nectarine tree the new variety is a white flat peach tree instead of a white nectarine tree. 'Nectarmagie' approximately ripens in the beginning of July, thus earlier than the new variety.

Compared to 'Flatpretty' (U.S. Plant Pat. No. 21,389) white flat peach tree, the new variety produces fruits of better presentation with a more regular shape, smoother skin, with a more luminous and more intense red coloration covering 95% of the fruit skin surface instead of 50-70% for 'Flatpretty'. The pistil cup is also better closed. A comparison of blooming and ripening periods' differences between the new variety and the 'Flatpretty' white flat peach variety is provided above.

DETAILED DESCRIPTION

Referring more specifically to the pomological details of this new and distinct variety of peach tree, the following was observed in 2008 and 2009 on trees in their third growing season, under the ecological conditions prevailing at the orchards located near the town of Elne, Pyrénées-Orientales departement, France. All observations have been done on rootstock cultivars. Used rootstocks were 'Franc Inra Montclar' (non-patented) trees or 'Cadaman' (non-patented) trees or 'INRA GF 677' (non-patented) trees. All major color code designations are by reference to The R.H.S. Colour Chart (Fourth Edition) provided by The Royal Horticultural Society of Great Britain.

Tree:

*Size.*—Generally. — Considered large. The tree size the first year was approximately 280 cm. The tree was pruned during each following dormant season to a height of approximately 250 cm. Current season shoots growth could reach 80 cm. The tree size from the second year (second and next years) reached a final height of 330 cm with current season shoots length comprised.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered vigourous. The present variety grew from about 200 cm to 280 cm in height during the first growing season. For second and following seasons, the variety was pruned to an approximate height of 250 cm.

*Productivity.*—Very Productive. Fruit set is spaced by thinning to develop the remaining fruit into the desired market sized fruit. The number of the fruit set varies with the prevailing climatic conditions and cultural practices employed during the bloom period, and is therefore not distinctive of the present variety.

*Bearer.*—Very regular. Thinning of 2 fruits out of 3 was necessary for the tree valorisation. Thinning was necessary every year during the years of observation.

*Form.*—The 'ASFPBF0796' variety has naturally a semi-spread to semi-upright shape.

*Density.*—Considered medium dense.

*Hardiness.*—The present tree was grown and evaluated in France. The variety had a good behavior under the central Pyrénées-Orientales departement typical climatic conditions and was selected for its hardiness. Experimentations on different sites with winter chilling requirement comprised between 350 hours and 1200 hours showed a good behaviour of the new variety in all cases. As a flat peach tree, the new variety should potentially be more sensitive to frosty conditions, low temperatures and climatic variations. However, the new variety pistil cup appeared to be little sensitive to cracking due to frosty conditions. The new variety is expected to be hardy in all zones adapted to the culture of peach trees.

Trunk:

*Diameter.*—Approximately about 6.5 cm in diameter when measured at a distance of approximately 30 cm above the soil level.

*Bark texture.*—Considered slightly rough, with folds of papery scarfskin being present.

*Lenticels.*—Numerous lenticels are present. The lenticels range in size from approximately 2.0 to 4.0 millimeters in width, and about 1.5 to 2.0 millimeters in height.

*Lenticel color.*—The outside of lenticels has a silver-grey color (RHS Grey 201 D or RHS Black 202 D), whereas the inside is considered brown (RHS Greyed Orange 166B).

*Bark coloration.*—The bark has a silver-grey color a little more pronounced than lenticels outside color (RHS Grey 201 C or RHS Black 202 C).

Branches:

*Size.*—Mature branches and current season shoots are considered medium for the variety.

*Diameter.*—Average as compared to other peach varieties. The current season shoots have a diameter from 5.0 to 7.0 millimeters, and observed branches have a diameter comprised between 15.0 and 22.0 millimeters.

*Surface texture.*—Average, wood which is several years old has no furrowed appearance.

*Crotch angles.*—Primary branches are considered variable, but the crotch angles are generally between 60 degrees and 80 degrees from the horizontal axis. This particular characteristic is not considered distinctive of the variety, however.

*Current season shoots.*—Surface texture. — Substantially glabrous.

*Internode length.*—Generally 22.0 millimeters to 30.0 millimeters.

*Color of mature branches.*—Grey brown (RHS Grey Brown 199 A to B).

*Current seasons shoots.*—Color. — The color of new shoot tips is considered a light green (RHS Green 144 A to C) on lower part of new shoot tips, whereas the upper part is colored in more or less brown-red (RHS Greyed Red 187 A to B or RHS Greyed Red 182 A to C).

Leaves:

*Size.*—Considered medium for the species. Leaf measurements have been taken from mature leaves in 2008. The ratio leaf length/leaf width is generally between 3.6 and 3.8.

*Leaf length.*—Approximately 165.0 millimeters without leaf petiole.

*Leaf width.*—Approximately 45.0 millimeters.

*Leaf base shape.*—Concave.

*Leaf form.*—Lanceolate.

*Leaf tip form.*—Acuminate and small.

*Leaf color.*—Upper leaf surface. — Dark Green (RHS Green 137 A). Lower surface. — Medium Green (RHS Green 137 B to 137 C).

*Leaf texture.*—Smooth, glabrous.

*Leaf venation.*—Pinnately veined.

*Mid-vein.*—Color. — Light green with a cream touch (RHS Yellow Green 145 D).

*Leaf margins.*—Slightly undulating.

*Form.*—Considered slightly dentate.

*Uniformity.*—Leaves are isolated or grouped by 2 or 3. In this last case, one leaf of normal size is found with one or two smaller leaves, which are at least 50% smaller than the normal leaf.

*Leaf petioles.*—Size. — Considered medium. Length. — Approximately between 8.0 and 12.0 mm. Diameter. — Approximately between 1.5 and 2.0 mm. Color. — Upper face is green (RHS Green Group 137 D to C) and lower face is yellow green (RHS Yellow Green 145 C to D).

*Leaf glands.*—Size. — Considered medium. Their length is about 2.0 millimeters. Number. — Generally 3 to 4. Type. — Reniform. Color. — On young leaves, leaf glands color is considered a pale green (RHS Green 145 B). On older leaves, leaf glands color turn to a dark brown (RHS Grey Brown 199 A to 199 B).

*Leaf stipules.*—Generally. — No leaf stipules were observed. But as seen in the characteristic relative to the leaves uniformity, it is possible to find leaves by groups of 2 or 3, with a normal-size leaf and smaller ones.

Flowers:

*Flower buds.*—Generally. — At pre-floral stage of development, the floral buds are conic in form with a round tip. Their form is evolving until blooming, with variables dimensions. Just before blooming, floral buds are approximately 11.0 millimeters wide and approximately 18.0 millimeters long.

*Flower buds.*—Color. — This characteristic is dependent upon the proximity to bloom. At pre-floral stage of development, the bottom of the flowers buds, formed by the sepals, is of purple-brown color (RHS Greyed Purple 183 A to C); the corolla, formed by the petals, is generally of medium pink color (varying from RHS Red Purple 65 A to C). Petals color shows an evolution until the end of flowering. The buds are considered hardy under typical central Pyrénées-Orientales departement climatic conditions.

*Hardiness.*—No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—Generally March. The first bloom was observed on Mar. 1, 2003.

*Blooming time.*—Considered of semi-early to semi-late season in relative comparison to other commercial peach cultivars grown in the Pyrénées-Orientales departement, France. The date of full bloom is observed on March. The date of bloom varies with climatic conditions and cultural practices. Thus the first full bloom was observed approximately on Mar. 6, 2003. Last observed blooming times were from Mar, 2, 2007 to Mar. 12, 2007, then from Feb. 21, 2008 to Feb. 29, 2008, then from Mar. 1, 2009 to Mar. 14, 2009.

*Duration of bloom.*—Approximately 12 days. This characteristic varies with the prevailing climatic conditions.

*Flower type.*—The variety is considered to have a showy type flower.

*Flower size.*—Considered medium. Flower diameter at full bloom is approximately between 28.0 and 34.0 millimeters.

*Bloom quantity.*—Considered abundant, approximately 40 and 45 flowers per meter.

*Flower bud frequency.*—Generally 2 flower buds appear per node, occasionally 1.

*Petal size.*—Generally. — Considered medium for the species.

*Length.*—Generally about 19.0 millimeters.

*Width.*—Generally about 18.0 millimeters.

*Petal form.*—Rounded.

*Petal count.*—Nearly always 5.

*Petal texture.*—Smooth and glabrous.

*Petal color.*—Medium Pink (RHS Red Purple 65 A to C) when young, slightly darkening with advancing senescence.

*Fragrance.*—Slight.

*Petal claw.*—Form. — The claw is considered to have a conic form with a slightly rounded extremity. Length. — Approximately 5.0 millimeters. Width. — Approximately 4.0 millimeters.

*Petal margins.*—Generally slightly undulated.

*Petal apex.*—Generally. — The petal apices have generally a wide-dome shape.

*Flower pedicel.*—Length. — Considered medium in length and having an average length of approximately 4.0 millimeters. Diameter. — Considered average, approximately 2.0 millimeters. Color. — A medium brown (RHS Grey Brown N199 C to D).

*Floral nectaries.*—Color. — A green yellow (RHS Yellow 13 A to B or RHS Yellow Green 150 A to B)

*Calyx.*—Internal surface texture. — Smooth, glabrous. Color. — The outer surface of the calyx is considered of Purple-brown (RHS Greyed Purple 183 B to D) color.

*Sepals.*—Form. — Oval. Surface texture. — The outer surface has a short, fine pubescent texture. Size. — Medium. Color. — Purple-brown (RHS Greyed Purple 183 B to D).

*Average number of stamens per flower.*—Approximately 40 stamens per flower.

*Anthers.*—Generally. — Medium in length. Color. — Yellow orange (RHS 16 A to B) browning after maturity to red to orange-red color (approximately RHS Greyed Purple 178 A).

*Pollen production.*—Pollen is abundant, and has a yellow color (Approximately RHS Yellow Orange 17 B to C). The present variety is considered self fruitful (self-pollinating).

*Filaments.*—Size. — Variable in length, approximately 11.0 to 19.0 millimeters in length. Filaments length is generally superior to the pistil's length.

*Color.*—Considered light pink (approximately RHS Red Purple 62 C to D) or pink (RHS Red Purple 73 A to B).

*Pistil.*—Number. — Usually 1. Generally. — Average in size. Length. — Approximately 13.0 to 16.0 millimeters including the ovary; Generally smaller to equal to filaments' length. Color. — Considered a very pale green (RHS Yellow Green 150 D or RHS Yellow Green 151 D). Surface texture. — Glabrous.

Fruit:

*Maturity when described.*—Very firm ripe condition (shipping ripe).

*Date of first picking.*—Jul. 25, 2003.

*Date of last picking.*—Aug. 4, 2003. The date of harvest varies slightly with the prevailing climatic conditions. The 'ASFPBF0796' variety has a semi-late date of picking, and a grouped maturity: only 2 harvests in approximately 10 days are generally necessary. Last known picking times were from Jul. 22 to Jul. 31, 2007, then from Jul. 21 to Jul. 31, 2008, then from Jul. 24 to Aug. 2, 2009.

*Size.*—Generally. — Considered medium to large, and homogeneous in size.

*Average cheek diameter.*—Approximately 70.0 to 80.0 millimeters.

*Average axial diameter.*—Approximately 35.0 to 42.0 millimeters.

*Typical weight.*—Generally around 170.0 grams. This characteristic is highly dependent upon the prevailing cultural practices, and therefore is not particularly distinctive of the variety.

*Fruit form.*—Generally. — Round and flattened. The fruit is generally uniform in symmetry, viewed from the suture's plane. Generally little dented.

*Fruit suture.*—Wide-mouthed, extending from the base to the apex. No apparent callousing or stitching exists along the suture line.

*Suture.*—Color. — The suture has generally a color similar to the whole fruit color: red (RHS Red Purple 61 A to B or RHS Red Group 47 C to D).

*Ventral surface.*—Form. — Smooth.

*Apex.*—Depressed.

*Base.*—Semi wide-mouthed, shallow.

*Stem cavity.*—Average depth of the stem cavity is about 0.7 cm. Average width is about 1.6 cm.

*Fruit skin.*—Thickness. — Considered thick and strong, and tenacious to moderately tenacious to the flesh depending on stage of maturity. Texture. — Almost not pubescent, very smooth for a peach variety. Taste. — Semi-sweet, very aromatic, with a high level of sugars. Tendency to crack. — Generally none.

*Color.*—Blush color. — This blush color is a luminous red (RHS Red Purple 61 A to B or Red Group 47 C to D). The red blush covers more than 95% of the fruit skin surface. Ground color. — Only on 5% of the whole fruit skin surface, and exclusively on the inferior part of the fruit: RHS Orange White Group 159 A to B.

*Fruit stem.*—Medium in length, approximately 6.0 millimeters.

*Diameter.*—Approximately 4.0 millimeters.

*Color.*—Pale green (RHS Yellow Green 145 A to 145 B).

*Flesh.*—Ripens. — Very evenly, slowly, long shelf-life. Texture. — Firm, very dense, crunchy, melting, juicy at harvest maturity stage. Fibers. — Generally not fibrous. Aroma. — Pronounced. Eating quality. — Considered very good, aromatic. Flavor. — Considered semi-sweet. The Brix is superior to 13 and acidity comprised between 6 and 9 meq/100 ml. The flavor is considered aromatic. Juice. — Very juicy at complete maturity. Brix. — Generally superior to 13.0 degrees in our area, but can be higher in very warm and sunny areas, such as Spain. This characteristic varies slightly with the number of fruit per tree; prevailing cultural practices; and the surrounding climatic conditions. Flesh color. — White flesh (RHS White Group N 155 D) with red pigmentation near the stone (RHS Red Purple 60 A to B).

Stone:

*Type.*—Semi-Clingstone.

*Size.*—Small. The stone size varies significantly depending upon the tree vigor, crop load and prevailing growing conditions.

*Length.*—Approximately 20.0 to 25.0 millimeters.

*Width.*—Approximately 20.0 to 24.0 millimeters.

*Diameter.*—Approximately 14.0 to 16.0 millimeters.

*Form.*—Flat.

*Base.*—Straight.

*Apex.*—Shape. — The stone apex is flat.

*Stone cavity.*—Considered small sized, with form and dimensions corresponding to the stone's dimensions.

*Stone surface.*—Surface texture. — The pit is transversely furrowed on its entire surface. Furrows are flatter and more pronounced on lateral faces. Ridges. — The surface texture is generally characterized by more prominent ridges along the ventral edges and is more prominent at the apical tip.

*Stone color.*—The color of the dry stone is generally considered an orange brown (RHS Greyed Orange 166 A to C).

*Tendency to split.*—Splitting is generally absent.

*Kernel.*—Size. — The kernel is considered small, about 7.0 mm long and 5.0 mm thick. Form. — Considered flat and elliptic. Occasionally double. Pellicle. — Slighlty pubescent. Color. — The kernel skin is a light orange-yellow (RHS Greyed Orange 166 C). The almond, which is the seed of the kernel, is cream-white (RHS Orange White 159 D). The kernel and its embryo are mature at the time of fruit maturity.

Use: The subject variety ASFPBF0796' is considered to be a peach tree of the semi-late season of maturity, and which produces fruits that are considered firm, attractively colored. Fruits have a semi-sweet taste and a very specific and developed flavor. They are excellent for uncooked consumption, crunchy or melting when at full maturity. Due to their flesh quality, firmness and density, and long shelf-life on the tree after growth completion and after harvesting they are useful for both local and very long distance shipping.

Keeping quality: Good. Fruits have a slow maturation and a long shelf-life both on the tree after growth completion and after harvesting. Storage was possible at 2.0 degree Celsius during approximately 2 weeks.

Shipping quality: Considered good. The fruit of the new peach variety showed minimal bruising of the flesh or skin damage after being subjected to normal harvesting and packing procedures. Its resistance to handling during harvest and packing and its long shelf life without alteration after harvest permit several weeks-shipping at 2 degrees Celsius.

Resistance to insects and disease: No particular susceptibilities were noted. The present variety is not very sensitive to powdery mildew, or conservation diseases and decay due to its thick and strong skin. The new variety pistil cup, well closed, appeared to be little sensitive to cracking.

Although the new variety of peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of flat peach tree as illustrated and described, characterized by fruits of very long shelf life without alteration before and after harvesting, and with a semi-sweet white flesh of high eating quality and an attractive skin, with a very high percentage of red blush.

* * * * *